(12) United States Patent
Auger et al.

(10) Patent No.: US 6,706,692 B1
(45) Date of Patent: Mar. 16, 2004

(54) 6-DEOXY ERYTHROMYCIN DERIVATIVES, METHOD FOR PREPARING SAME AND USE AS MEDICINES

(75) Inventors: Jean-Michel Auger, deceased, late of Montreuil (FR); by Pierre Michel Auger, heir, Pessac (FR); by Nicole Noelle DeJean, heir, Pessac (FR); by Catherine Laurence Auger, heir, Pessac (FR); Alexis Denis, Paris (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/744,320

(22) PCT Filed: Jul. 20, 1999

(86) PCT No.: PCT/FR99/01769

§ 371 (c)(1),
(2), (4) Date: Apr. 10, 2001

(87) PCT Pub. No.: WO00/05239

PCT Pub. Date: Feb. 3, 2000

(30) Foreign Application Priority Data

Jul. 21, 1998 (FR) .............................. 98 09259

(51) Int. Cl.[7] .................. A61K 31/70; C07H 17/08
(52) U.S. Cl. ..................... 514/29; 536/7.2; 536/7.4
(58) Field of Search ................... 536/7.4, 7.2; 574/29

(56) References Cited

U.S. PATENT DOCUMENTS

| 5,543,400 | A | * | 8/1996 | Agouridas et al. | 514/29 |
| 5,747,466 | A | * | 5/1998 | Elliott et al. | 574/29 |
| 5,747,467 | A | * | 5/1998 | Agouridas et al. | 574/29 |
| 6,096,714 | A | * | 8/2000 | Agouridas et al. | 574/29 |
| 6,399,582 | B1 | * | 6/2002 | Hlasta et al. | 514/29 |

FOREIGN PATENT DOCUMENTS

| FR | 2692579 | 12/1993 |
| WO | 9731929 | 9/1997 |
| WO | 9742205 | 11/1997 |
| WO | 9803530 | 1/1998 |

OTHER PUBLICATIONS

Griesgraber et al, "3–Keto–. . . Vitro Activity", Journal of Antibiotics, vol. 49, No. 5, May 1996 pp. 465–477.

* cited by examiner

*Primary Examiner*—Elli Peselev
(74) *Attorney, Agent, or Firm*—Muserlian, Lucas and Mercanti

(57) ABSTRACT

The invention concerns compounds of formula (I) wherein: X represents a (NH)a, $CH_2$ or $SO_2$ radical or an oxygen atom; a represents 0 or 1; Y represents a $(CH_2)m$-$(CH=CH)n$-$(CH_2)o$ radical with $m+n+o \leq 8$, $n=0$ or 1; Ar represents an aryl or heteroaryl radical, optionally substituted; W represents a hydrogen atom or a halogen atom; Z represents a hydrogen atom or an acid residue, and their addition salts with acids. The compounds of formula (I) have antibiotic properties

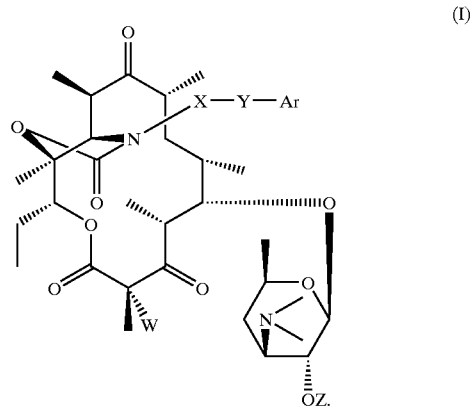

15 Claims, No Drawings

6-DEOXY ERYTHROMYCIN DERIVATIVES, METHOD FOR PREPARING SAME AND USE AS MEDICINES

This application is a 371 of PCT/FR99/01769 filed Jul. 20, 1999.

The present invention relates to new derivatives of 6-deoxy erythromycin, their preparation process and their use as medicaments.

10-methyl 6-methoxy 3-oxo derivatives of erythromycin are known (cf. WO 98/03530. 6-demethoxy 10-demethyl erythromycin derivatives are also known (cf. FR A-2692579). erythromycin 3,11,12-trihydroxy derivatives which are used as intermediates in the synthesis of antibiotic products are also known (cf. WO 97/42205).

A subject of the invention is the compounds of formula (I)

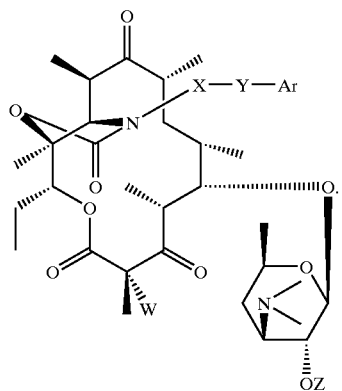

in which
X represents an (NH)a, CH$_2$ or SO$_2$ radical or an oxygen atom, a represents the number 0 or 1,
Y represents a (CH$_2$)m-(CH=CH)n-(CH$_2$)o radical with m+n+o≦8, n=0 or 1,
Ar represents an aryl or heteroaryl radical, optionally substituted
W represents a hydrogen atom or a halogen atom
Z represents a hydrogen atom or the remainder of an acid as well as their addition salts with acids.

Among the addition salts with acids, there can be mentioned the salts formed with the following acids: acetic, propionic, trifluoroacetic, maleic, tartaric, methanesulphonic, benzenesulphonic, p-toluenesulphonic and especially stearic, ethylsuccinic, or laurylsulphonic acids.

The aryl radical is preferably a phenyl or naphthyl radical. methanesulphonic, benzenesulphonic, p-toluenesulphonic and especially stearic, ethylsuccinic, or laurylsulphonic acids.

The aryl radical is preferably a phenyl or naphthyl radical.

The heteroaryl can be thienyl, furyl, pyrolyl, thiazolyl, oxazolyl, imidazolyl radical, for example the 4-(3-pyridinyl) 1H-imidazolyl, thiadiazolyl, pyrazolyl or isopyrazolyl radical, a pyridyl, pyrimidyl, pyridazinyl or pyrazinyl radical, or also an indolyl, benzofurannyl, benzothiazyl or quinolinyl radical.

These aryl radicals can be substituted by one or more groups chosen from the group constituted by the hydroxyl, the halogen atoms, the NO$_2$ radicals, the C≡N, the alkyl, alkenyl or alkynyl, O-alkyl, O-alkenyl or O-alkynyl, S-alkyl, S-alkenyl or S-alkynyl and N-alkyl, N-alkenyl or N-alkynyl radicals, containing up to 12 carbon atoms optionally substituted by one or more halogen atoms, the

radical
R$_a$ and R$_b$ identical or different representing a hydrogen atom or an alkyl radical containing up to 12 carbon atoms, the

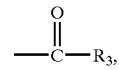

R$_3$ representing an alkyl radical containing up to 12 carbon atoms, aryl or heteroaryl with 5 or 6 mng members and comprising one or more heteroatoms, optionally substituted by one or more of the substituents mentioned above.

As preferred heterocycle, there can be mentioned amongst others

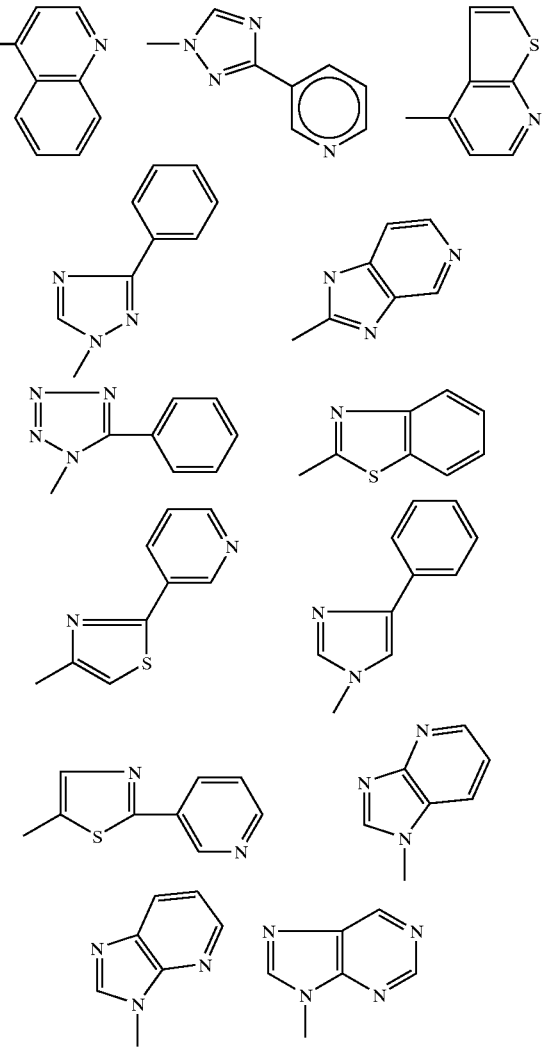

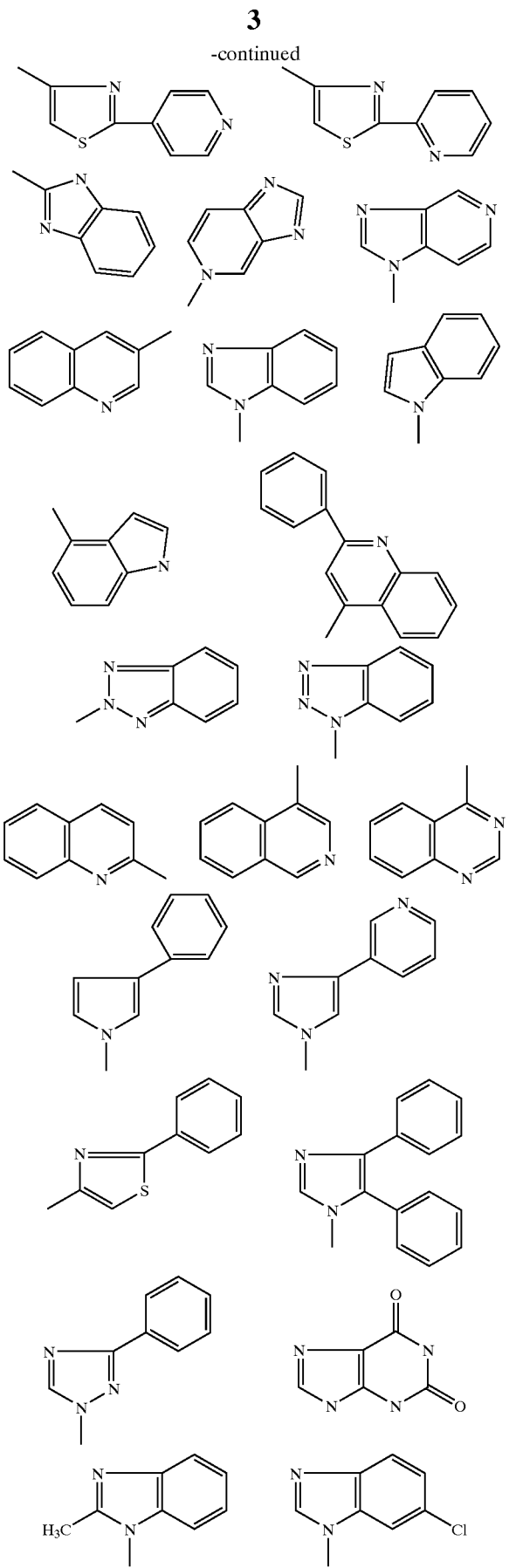

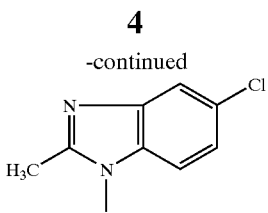

and the heterocyclic radicals envisaged in the European Patent Applications 487411, 596802, 676409 and 680967. These preferred heterocyclic radicals can be substituted by one or more functional groups.

Hal preferably represents a fluorine, chlorine or bromine atom.

Among the preferred compounds of the invention, there can be mentioned those in which Z represents a hydrogen atom, those in which W represents a hydrogen atom, those in which X represents a $CH_2$ radical, those in which Y represents a $(CH_2)_3$ or $(CH_2)_4$ radical, and in particular those in which Ar represents the

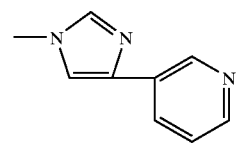

radical.

A quite particular subject of the invention is the product of Example 1.

The products of general formula (I) have a very good antibiotic activity on gram ⊕ bacteria such as staphylococci, streptococci, pneumococci.

The compounds of the invention can therefore be used as medicaments in the treatment of germ-sensitive infections and in particular, in that of staphylococcia such as staphylococcal septicaemias, malignant staphylococcia of the face or skin, pyodermitis, septic or suppurating wounds, boils, phlegmons, erysipelas and acne, staphylococcia such as primitive or post-influenzal acute angina, bronchopneumonia, pulmonary suppuration, streptococcia such as acute angina, otitis, sinusitis, scarlatina, pneumococcia such as pneumonia, bronchitis, brucellosis, diphtheria, gonococcal infection.

The products of the present invention are also active against infections caused by germs such as Haemophilus influenzae, Rickettsia, Mycoplasma pneumoniae, Chlamydia, Legionella, Ureaplasma, Toxoplasma, or germs of the Mycobacterium genus.

Therefore, a subject of the present invention is also the products of formula (I) as defined above, as well as their addition salts with the pharmaceutically acceptable mineral or organic acids, as medicaments and, in particular antibiotic medicaments.

A more particular subject of the invention is the products of the examples and their pharmaceutically acceptable salts, as medicaments and, in particular antibiotic medicaments.

A subject of the invention is also the pharmaceutical compositions containing at least one of the medicaments defined above, as active ingredient.

These compositions can be administered by buccal, rectal, parenteral route, or by local route as a topical application on the skin and mucous membranes, but the preferred administration route is the buccal route.

They can be solids or liquids and be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated with the excipients usually used in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example, apyrogenic sterile water.

The dose administered is variable according to the affection treated, the patient in question, the administration route and the product considered. It can be, for example, comprised between 50 mg and 300 mg per day by oral route for an adult for the product of Example 1.

A subject of the invention is also a preparation process characterized in that a compound of formula (II), (II)

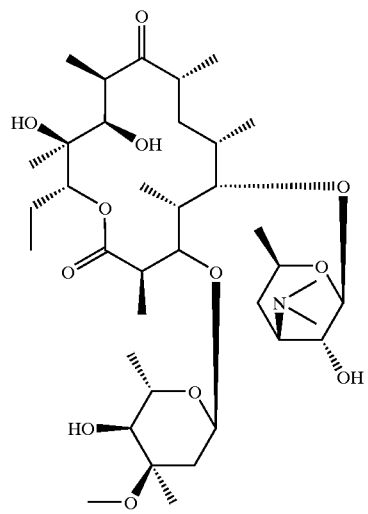

is subjected to the action of a cladinose hydrolysis agent in aqueous medium in order to obtain the compound of formula (III), (III)

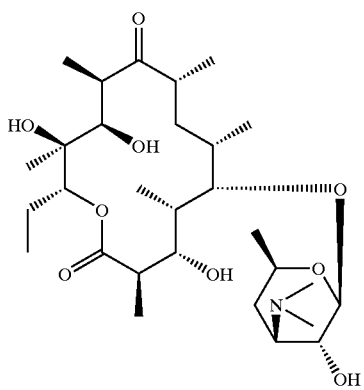

which is subjected to the action of a blocking agent of the hydroxyl function in position 2' in order to obtain a compound of formula (IV):

(IV)

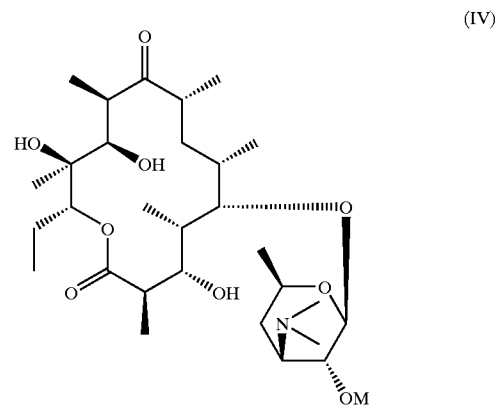

in which OM represents a blocked hydroxyl group which is subjected to the action of an oxidizing agent of the hydroxyl group in position 3 in order to obtain the compound of formula (V):

(V)

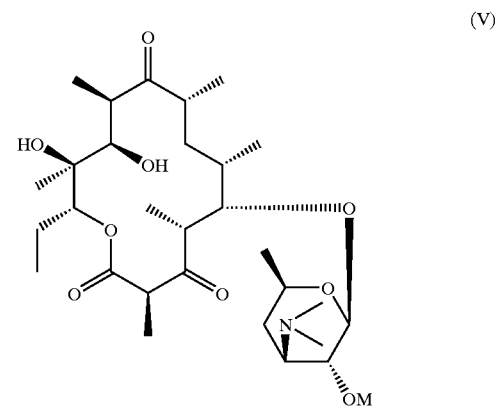

then if desired, the hydroxyl in position 2' is released in order to obtain the compound of formula (VI):

(VI)

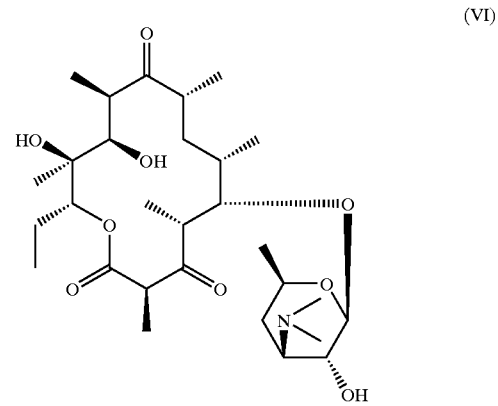

then if desired any one of products (V) or (VI) is subjected to the action of an agent capable of creating a double bond in position 11, 12 in order to obtain the compound of formula (VII)

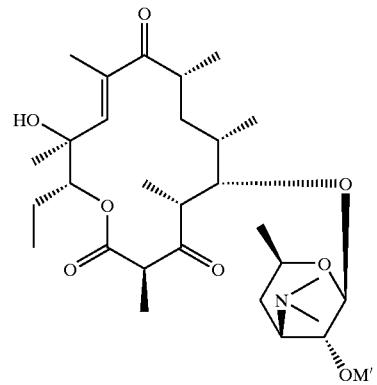

(VII)

in which OM' represents a free or blocked hydroxyl radical which is subjected to the action of carbonyldiimidazole in order to obtain the compound of formula (VIII):

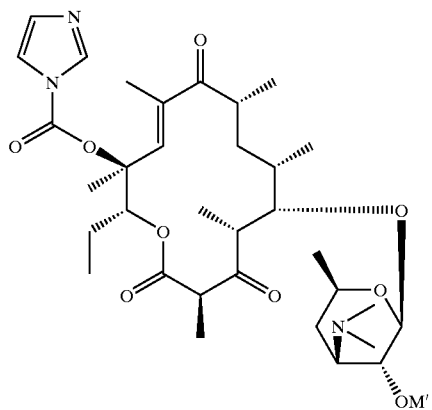

(VIII)

which is subjected to the action of a compound of formula ArYXNH$_2$ in which Y, X and Ar have the meaning indicated previously in order to obtain the corresponding compound of formula (IA)

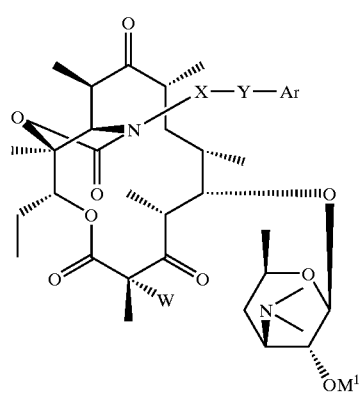

(IA)

in which W represents a hydrogen atom which is subjected if desired to the action of a halogenation agent in order to obtain the compound of formula (IB) in which W represents a halogen atom,

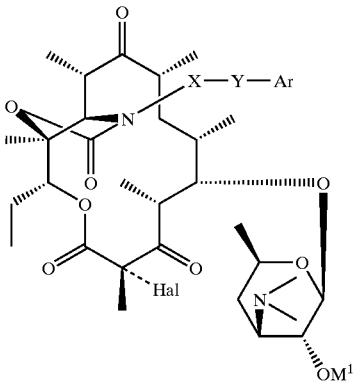

(IB)

then if desired the hydroxyl in position 2' is released and/or if appropriate subjected to the action of an acid in order to form the salt.

The compounds of formula (II) used as starting products of the process of the invention are known products described for example in EP 0216169, EP 41355 and EP 0180415.

Hydrolysis of cladinose is carried out using aqueous hydrochloric acid or in methanol.

Blocking of the hydrolysis in position 2' is carried out by using an acid or a functional derivative of an acid for example an acid anhydride, an acid halide or silicon derivatives.

Oxidation of the hydroxyl in position 3 is carried out by using diimides in the presence of dimethylsulphoxide DMSO.

The product of formula (V) or (VI) is firstly converted to a carbonate in position 11, 12, by the action of CDI and DBU, which is converted to product (VII) by agitation at 30° C.±5° C.

Reaction of compound (VIII) with ArYXNH$_2$ takes place in a solvent such as for example acetonitrile, dimethyl formamide or also tetrahydrofuran, dimethoxyethane or dimethylsulphoxide.

Hydrolysis of the ester function in position 2' is carried out using methanol or aqueous hydrochloric acid.

Salification is carried out using an acid according to standard processes.

The halogenation in position 2 is for example a fluoridation, which can be carried out by use of the compound of formula

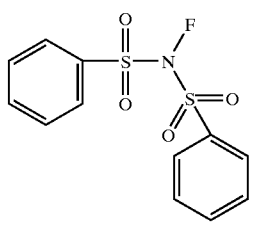

(I)

The compounds of formulae (V), (VI), (VII) and (VIII) used during the process are new and are in themselves a subject of the present invention.

The following examples illustrate the invention without however limiting it.

EXAMPLE 1

3-de-[(2,6-dideoxy-3-C-methyl-3-O-methyl-alpha-L-ribo-hexopyranosyl)-oxy]-3-oxo-12,11-[oxycarbonyl[[4-[4-(3-pyridinyl)-1H-imidazol-1-yl]butyllimino)]-6,11,12-trideoxy-erythromycin and (10S) 3-de-[(2,6-dideoxy-3-C-methyl-3-O-methyl-alpha-L-ribo-hexopyranosyl)-oxy]-3-oxo-12,11-[oxycabonyl[[4-[4-(3-pyridinyl)-1H-imidazol-1-yl]butyl]imino]]-6,11,12-trideoxy-erythromycin Stage A: 6-deoxy-3-O-de(2,6-dideoxy-3-C-methyl-.alpha.-L-ribohexo-pyranosyl)-erythromycin 100 ml of demineralized water, 50 ml of a normal solution of hydrochloric acid and 9.58 g of a mixture of 6,12-dideoxy-erythromycin and 3"-O-demethyl-6,12-dideoxy-erythromycin is agitated at ambient temperature for 3 hours.

After extracting with ethyl acetate and washing with water, the aqueous phases are collected then poured into a solution of ammonium hydroxide at 10° C., followed by extracting with ethyl acetate, washing with water, drying, filtering and concentrating. The product obtained is purified by chromatography on silica eluting with a $CH_2Cl_2$/MeOH/$NH_4OH$ mixture (95-5-0.5). The fractions of rf=0.4 are recovered. In this way 0.246 g of sought product is obtained.

Stage B: 6-deoxy-3-O-de(2,6-dideoxy-3-C-methyl-3-O-methyl-alpha-L-ribohexopyranosyl)-erythromycin 2'-acetate A solution of 18 ml of ethyl acetate, 0.42 ml of acetic anhydride and 1.755 g of the product of Stage A is agitated for 1 hour 45 minutes at ambient temperature. The reaction medium is poured into water, the pH is adjusted to 9/10 with a saturated solution of sodium carbonate, followed by extracting with ethyl acetate, washing with an aqueous solution of sodium carbonate then with water, drying, filtering and concentrating. In this way 1.826 g of sought product is obtained.

Stage C: 6-deoxy-3-de[(2,6-dideoxy-3-C-methyl-3-O-methyl-alpha-L-ribohexopyranosyl)oxy]-3-oxo-erythromycin 2'-acetate 3.45 g of 1-ethyl-3-(3-dimethylaminopropyl) carbodiimide hydrochloride is introduced at ambient temperature into a solution containing 55 ml of methylene chloride and 3.5 ml of DMSO. The reaction medium is agitated at ambient temperature for 25 minutes. Then 1.82 g of the product of the previous stage is introduced, followed by agitation for 15 minutes. After cooling down to 15° C., 3.47 g of pyridinium trifluoroacetate in 25 ml of methylene chloride is added. Agitation is carried out for 30 minutes, followed by purifying by chromatography on silica eluting with a propopyl ether/isopropanol/TEA mixture (8-1-1). (rf=0.38). After washing with ammonium hydroxide in ethyl acetate and drying 156 mg of sought product is obtained.

Stage D: 6-deoxy-3-O-de-[(2,6-dideoxy-3-C-methyl-3-O-methyl-alpha-L-ribohexopyranosyl)-oxy]-3-oxo-erythromycin A solution containing 0.5 ml of methanol and 61 mg of the product of Stage C is agitated at 5° C. for 40 hours. The reaction medium is returned to ambient temperature, followed by agitating for 8 hours at ambient temperature and evaporating the solvent. The product obtained is chromatographed on silica, eluent $CH_2Cl_2$/isopropanol/$NH_4OH$(94-4-0.5). 14 mg of sought product is obtained.

Stage E: 6-deoxy-3-de[[(2,6-dideoxy-3-C-methyl-3-O-methyl-.alpha.-L-ribo-hexopyranosyl)oxy]-3-oxo-erythromycin cyclic 2'-acetate and 11,12-carbonate and 10,11-didehydro-6,11-dideoxy-3-de[2,6-dideoxy-3-C-methyl-3-O-methyl-alpha-L-ribo-hexopyranosyl)oxy]-3-oxo-erythromycin 2'-acetate A solution of 3.5 ml of ethyl acetate, 0.346 g of the product of Stage C, 9 µl of DBU, 0.127 g of 1.1' carbonyl-diimidazole is agitated for 5 hours at ambient temperature. Then agitation is carried out for 15 hours at 30° C., followed by pouring into water, extracting with ethyl acetate, washing with water, drying, filtering and concentrating. 0.301 g of product is obtained which is chromatographed on silica eluting with a methylene chloride, isopropanol, ammonium hydroxide mixture 95-5-05. The fractions which are homogeneous as regards TLC are concentrated, taken up in ethyl acetate, dried, filtered and concentrated. 0.162 g of sought product is obtained.

Stage F: 10,11-didehydro-6,11-dideoxy-3-de[(2,6-dideoxy-3-C-methyl-3-0-methyl-alpha-L-ribo-hexopyranosyl)-oxy]-3-oxo-erythromycin 2'-acetate and 12-[(1H-imidazol-1-yl)carboxylate]

A solution containing 2 ml of THF, 0.155 g of the product of the previous stage, 6 µl of DBU and 0.064 g of 1,1'carbonyldiimidazole is agitated at 0C for 3 hours. Then agitation is carried out for 15 hours at 10° C., followed by pouring into water, extracting with ethyl acetate, washing with water, drying, filtering and concentrating. In this way the sought product is obtained.

Stage G: 3-de[2,6-dideoxy-3-C-methyl-3-0-methyl-alpha-L-ribo-hexopyranosyl)-oxy]-3-oxo-12,11-[oxycarbonyl[[4-[4-(3-pyridinyl)-1H-imidazol-1-yl]-butyl]-imino]]-6,11,12-trideoxy-erythromycin (product A) and (10S) 3-de[2,6-dideoxy-3-C-methyl-3-0-methyl-.alpha.-L-ribo-hexopyranosyl)oxy]-3-oxo-12,11-[oxycarbonyl[[4-[4-(3-pyridinyl)-1H-imidazol-1-yl]butyl]imino]]-6,11,12-trideoxy-erythromycin (product B)

A solution containing 1.5 ml of acetonitrile, 0.15 ml of water, 0.17 g of the product of the previous stage and 0.199 g of 4-(3-pyridinyl)1H-imidazol-1-butanamine is agitated for 4 hours at 60° C. The reaction medium is poured into water, followed by extracting with ethyl acetate, washing with water, drying, filtering and concentrating. 0.184 g of product is obtained which is poured into a solution of 2 ml of methanol and 25 µl of DBU. Agitation is carried out for 16 hours at ambient temperature, followed by evaporating the methanol, chromatographing on silica eluting with a methylene chloride/methanol/ammonium hydroxide mixture (93-7-0.5). The fraction of rf=0.38 is collected, washed with ammonium hydroxide in ethyl acetate and dried over magnesium sulphate. 37 mg of product A is obtained. The fraction of rf=0.36 is also collected, it is purified again by chromatography on silica eluting with a methylene chloride/methanol/ammonium hydroxide mixture (93-7-1), followed by washing with a methylene chloride, isopropanol, ammonium hydroxide mixture 9-1-0,5- and concentrating. The residue is taken up in methylene chloride, dried, filtered and concentrated. 13 mg of product B is obtained.

EXAMPLES OF PHARMACEUTICAL COMPOSITIONS

Tablets were prepared containing:

| Product of Example 1 | 150 mg |
|---|---|
| Excipient q.s. for. | 1 g |

Detail of excipient: starch, talc, magnesium stearate

Infectible solutions were also prepared from salified products.

PHARMACOLOGICAL STUDY OF THE PRODUCTS OF THE INVENTION

A—Method of Dilutions in Liquid Medium

A series of tubesis prepared in which the same quantity of nutritive sterile medium is distributed. Increasing quantities of the product to be studied are distributed into each tube, then each tube is sown with a bacterial strain. After incubation for twenty-four hours in a heating chamber at 37° C., the growth inhibition is evaluated by transillumination, which allows the minimal inhibitory concentrations (M.I.C.) to be determined, expressed in micrograms/cm³.

The following results were obtained with the product of the example: (reading after 24 hours)

| S. aureus | 011UC4 | 0.300 |
|---|---|---|
| S. agalactiae | 02B1HT1 | <+0.02 |
| E. faecalis | 02D2UC1 | 0.080 |
| E. faecium | 02D3HT1 | 0.040 |
| Streptococcus gr;G | 02GOGR5 | 0.040 |
| S. mitis | 02MitCB1 | 0.040 |
| S. pyogenes | 02A1SJc | |
| S. agalactiae | 02B1SJ1c | 2.500 |
| Streptococcus gr.G | 02Gogr4c | |
| S. mitis | 02MitGR16i | 0.300 |
| S. pneumoniae | 032UC1 | <=0.02 |
| S. pneumoniae | 030GR20 | 0.600 |
| S. pneumoniae | 030SJ5i | 0.600 |
| S. pneumoniae | 030CR18c | |
| S. pneumoniae | 030PW23c | 0.300 |
| S. pneumoniae | 030RO1i | 0.600 |

What is claimed is:

1. A compound selected from the group consisting of a compound of the formula

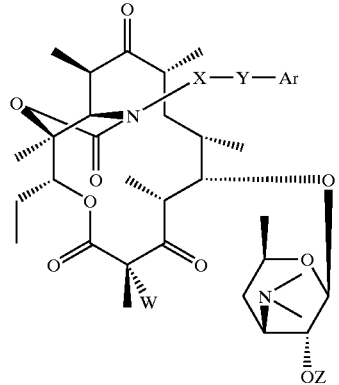

I wherein X is selected from the group consisting of —(NH)$_a$—, —CH$_2$—, —SO$_2$ and —O—, a is 0 or 1, Y is —(CH$_2$)$_m$—(CH=CH)$_n$—(CH$_2$)$_o$—, n is 0 or 1, m+n+o≦8, Ar is aryl or heteroaryl each unsubstituted or substituted with at least one member of the group consisting of a) —OH, halogen, —NO$_2$, —CN, b) alkyl, alkenyl, alkynyl, —Oalkyl, —Oalkenyl, —Oalkynyl, —Salkyl, —Salkenyl, —Salkynyl, —Nalkyl, —Nalkenyl and —Nalkynyl, all of up to 12 carbon atoms, c)

with R$_a$ and R$_b$ being individually hydrogen or alkyl of up to 12 carbon atoms and d)

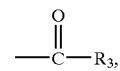

R$_3$ is selected from the group consisting of unsubstituted or substituted alkyl of up to 12 carbon atoms, aryl and heteroaryl, heteroaryl having 5 to 6 ring members and containing at least one heteroatom, W is hydrogen or halogen, Z is hydrogen or acyl and its non-toxic, pharmaceutically acceptable acid addition salts.

2. A compound of claim 1 wherein Z is hydrogen.

3. A compound of claim 1 wherein W is hydrogen.

4. A compound of claim 1 wherein X is —CH$_2$—.

5. A compound of claim 1 wherein Y is —(CH$_2$)$_3$ or —(CH$_2$)$_4$.

6. A compound of claim 1 wherein Ar is

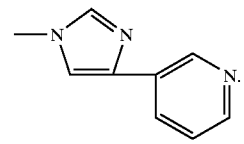

7. A compound of the formula selected from the group consisting of

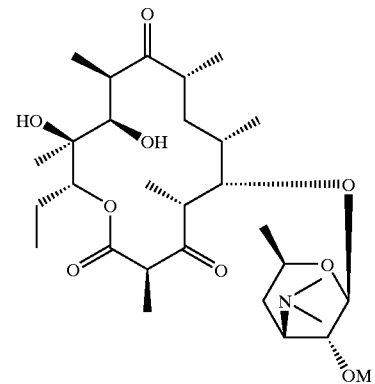

V

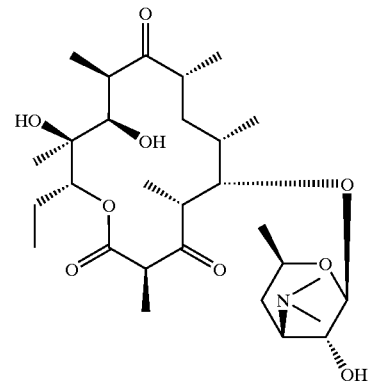

VI

VII

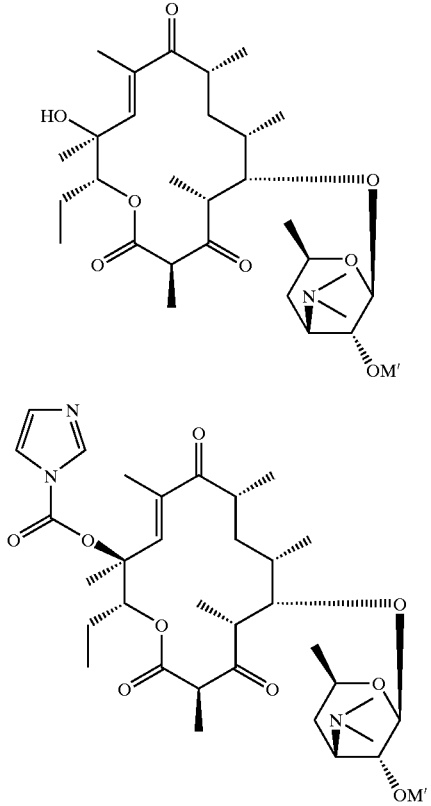

wherein —OM is a protected hydroxyl and —OM' is a free or protected hydroxyl.

8. A method of treating bacterial infections in warm-blooded animals comprising administering to warm-blooded animals in need thereof an antibacterially effective amount of a compound of claim 1.

9. The method of claim 8 wherein Z is hydrogen.

10. The method of claim 8 wherein W is hydrogen.

11. The method of claim 8 wherein X is —CH$_2$—.

12. The method of claim 8 wherein Y is —(CH$_2$)$_3$— or —(CH$_2$)$_4$—.

13. A compound of claim 1 which is 3-de[(2,6-dideoxy-3-C-methyl-3-0-methyl-alpha-L-ribo-hexopyranosyl)oxy]-3-oxo-12,11-[oxycarbonyl [[4-(4-(3-pyridinyl)-1H-imidazol-1-yl] butyl] imino]]-6, 11,12-trideoxy-erythromycin.

14. Process for the preparation of compounds of formula (I) defined in claim 1, characterized in that a compound of formula (II):

II

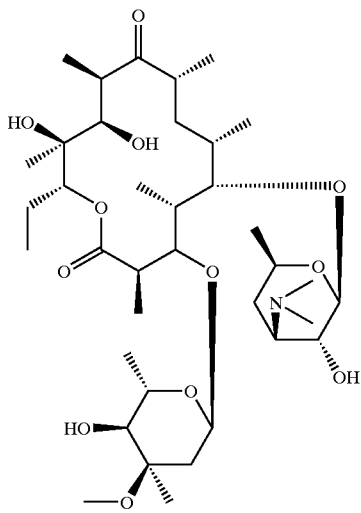

is subjected to the action of a cladinose hydrolysis agent in aqueous medium in order to obtain the compound of formula (III):

III

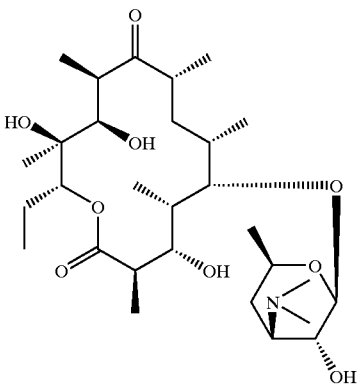

which is subjected to the action of a blocking agent of the hydroxyl function in position 2' in order to obtain a compound of formula (IV):

IV

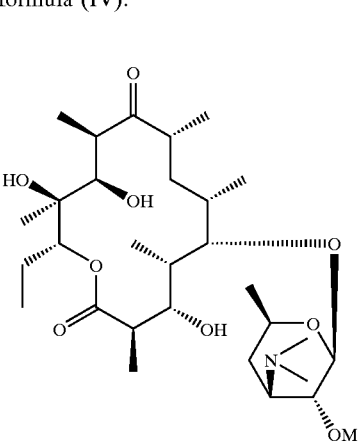

in which OM represents a blocked hydroxyl group which is subjected to the action of an oxidizing agent of the hydroxyl group in position 3 in order to obtain the compound of formula (V):

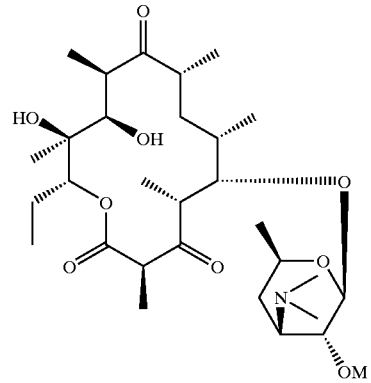

then if desired the hydroxyl in position 2' is released in order to obtain the compound of formula (VI):

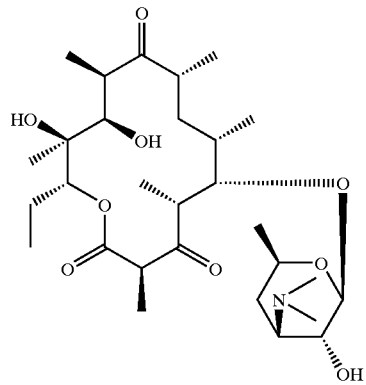

then if desired any one of products (V) or (VI) is subjected to the action of an agent capable of creating a double bond in position 11, 12 in order to obtain the compound of formula (VII):

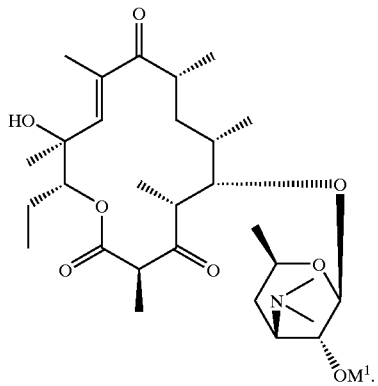

in which OM' represents a free or blocked hydroxyl radical which is subjected to the action of carbonyldiimidazole in order to obtain the compound of formula (VIII):

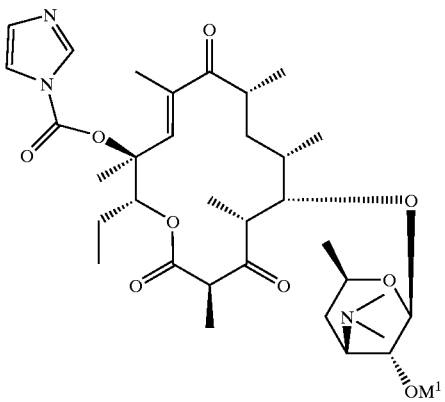

which is subjected to the action of a compound of formula $ArYXN_2$ in which Y, X, and Ar have the meaning indicated in claim 1, in order to obtain the corresponding compound of formula (IA):

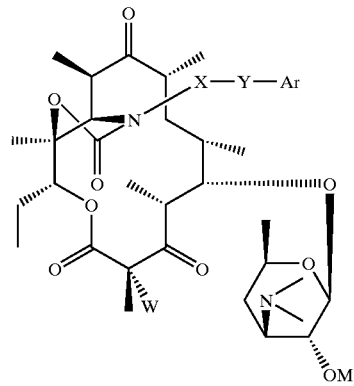

in which W represents a hydrogen atom which is subjected if desired to the action of a halogenation agent in order to obtain the compound of formula (IB) in which W represents a halogen atom,

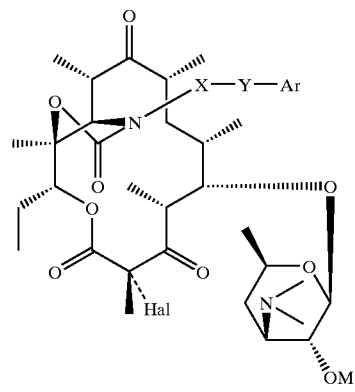

then if desired the hydroxyl in position 2' is released and/or if appropriate subjected to the action of an acid in order to form the salt.

15. A bactericidal composition comprising a bactericidally effective amount of a compound of claim 1 and an inert pharmaceutical carrier.

* * * * *